United States Patent [19]

Venturello et al.

[11] Patent Number: 4,595,671
[45] Date of Patent: Jun. 17, 1986

[54] PEROXIDE COMPOSITIONS BASED ON TUNGSTEN AND PHOSPHORUS OR ARSENIC, AND PROCESSES AND USES RELATIVE THERETO

[75] Inventors: Carlo Venturello; Rino D'Aloisio; Marco Ricci, all of Novara, Italy

[73] Assignee: Montedison S.p.A., Milan, Italy

[21] Appl. No.: 781,749

[22] Filed: Sep. 30, 1985

Related U.S. Application Data

[62] Division of Ser. No. 550,620, Nov. 10, 1983, Pat. No. 4,562,276.

[30] Foreign Application Priority Data

Nov. 10, 1982 [IT] Italy ............................... 24154 A/82

[51] Int. Cl.⁴ .............................................. B01J 31/06
[52] U.S. Cl. .................................... 502/159; 502/160; 502/164
[58] Field of Search .................... 502/159, 160, 164

[56] References Cited

U.S. PATENT DOCUMENTS

| | | | |
|---|---|---|---|
| 3,434,975 | 3/1969 | Sheng et al. | 502/160 |
| 3,453,218 | 7/1969 | Sheng et al. | 502/160 |
| 3,573,226 | 3/1971 | Sorgenti | 502/160 |
| 3,597,459 | 7/1971 | Mimoun et al. | 502/160 X |
| 3,953,362 | 4/1976 | Lines et al. | 502/160 |
| 4,171,313 | 10/1979 | Mares et al. | 549/272 |

OTHER PUBLICATIONS

76 *Topics in Current Chemistry*, "Aspects of Molybdenum and Related Chemistry", pub. by Springer-Veluag (1978), pp. 4–8.

*Advanced Inorganic Chemistry*, pub. by Interscience Publishers, Third Edition, pp. 952–953.
*The Chemistry of Chromium, Molybdenum and Tungsten*, Chapter 36 of Comprehensive Inorganic Chemistry, pub. by Pergamon Press, pp. 767–768.

*Primary Examiner*—Patrick P. Garvin
*Attorney, Agent, or Firm*—Stevens, Davis, Miller & Mosher

[57] ABSTRACT

Compositions of formula (I):

$$Q_3XW_4O_{24-2n} \qquad (I)$$

wherein:
Q represents a cation of an "onium" salt;
X is either a P or an As atom; while
n is 0, 1 or 2.

The preparative method consists in reacting an oxygenated tungsten (VI) derivative, an oxygenated P (V) or As (V) derivative, and hydrogen peroxide, in an aqueous acid phase, with and "onium" salt or a precursor thereof, if desired contained in an organic phase immiscible with the aqueous phase, at substantially room temperature. The oxygenated compounds of W (VI), P (V) or As (V) may be prepared "in situ" under the conditions of the reaction.

Compositions (I), which appear as solids or as viscous oils, find use as oxidizing agents in general in oxidation processes, and especially as epoxidation catalysts for olefinic compounds, both in a homogeneous phase as well as in a heterogeneous phase, and preferably according to the phase-transfer technique, in the presence of oxidizing agents.

2 Claims, No Drawings

PEROXIDE COMPOSITIONS BASED ON TUNGSTEN AND PHOSPHORUS OR ARSENIC, AND PROCESSES AND USES RELATIVE THERETO

This is a Division of application Ser. No. 550,620 filed Nov. 10, 1983 and now U.S. Pat. No. 4,562,276.

The present invention relates to new peroxidic compositions based on tungsten and phosphorus, or tungsten and arsenic.

More particularly, the present invention relates to peroxidic compositions based on tungsten and phosphorus or arsenic, and cationic groups derived from "onium" salts.

The invention relates moreover to the method of preparing the above-mentioned compositions, defined in more detail further on, and to various applications for them, especially as epoxidation catalysts.

More particularly, the present invention is directed to peroxidic compositions based on tungsten chemically associated with phosphorus or arsenic and with quaternary cations.

To the said compositions there may be ascribed the following rough formula (I):

$$Q_3XW_4O_{24-2n} \quad (1)$$

wherein:
Q represents an "onium" salt cation, defined in more detail further on;
X represents a P or As atom; while
n is a number chosen between 0, 1 and 2.

The above compositions may appear either in solid crystalline form or in the form of viscous oils.

They are obtained starting from a suitable oxygenated tungsten derivative and from a suitable phosphorus or arsenic oxygenated derivative, by reaction with hydrogen peroxide and an "onium" salt, according to a method which likewise is an object of the present invention.

The compositions of the above-defined formula (I) are believed to be new in and of themselves and, within the scope of formula (I), are considered to be structurally formed by an anionic complex that comprises tungsten with phosphorus or arsenic, and by "onium" cations, as defined in more detail further on.

The compositions which are an object of the present invention may be defined as the products resulting from the reaction of the above-mentioned starting compounds, under the operational conditions that will be indicated further on, and, thus, the above suggested structure must be understood as being a reasonable supposition within the scope of formula (I) which defines the compositions themselves without any limitation on their scope.

The compositions thus obtained, whether oily liquid or solid, represent useful compounds having interesting applications.

In fact, thanks to the active oxygen present in them, these compositions may be used as oxidizing agents in general, and especially, for instance, in epoxidation reactions of compounds having olefinic bonds, with respect to which compounds they show a considerable epoxidizing activity.

More particularly, when they are used as reactants the compositions of this invention make it possible to prepare epoxides starting from olefines. Or, used in small quantities, they constitute excellent catalysts in a homogeneous phase or, according to the phase-transfer technique, for the catalytic epoxidation of unsaturated compounds carried out with the help of oxidizing agents, such as for instance hydrogen peroxide.

In this connection, the compositions of formula (I), as previously defined, may be represented also by the following equivalent formula:

$$Q_3XW_4O_{16}(O_{act})_{2m}$$

in which: m is an integer chosen from amongst 2, 3 or 4, while the subscript "act" stands for the word "active", the other symbols having the meanings given above.

The epoxidized (=epoxy) compounds thus obtained, such as the epoxides (=epoxy compounds) of olefines, are chemical products of a considerable economical importance, which find applications in industry sometimes on a large scale.

In fact, besides as useful intermediates for organic syntheses in general, amongst the main possible applications there by be listed those as intermediates in the production of urethanes, in the industry of foamed materials, of glycols for lubricants, of surfactants, of esters for plasticizers, of polyester resins, etc. Lastly, the epoxides may find a direct application in the preparation of thermosetting epoxy resins, etc.

Organo-metal complexes of molybdenum and of tungsten have been described as catalysts suited for the epoxidation of olefinic bonds with hydrogen peroxide, for instance molybdenum or tungsten complexes with amides of carboxylic acids or mineral acids; or containing organic binders, which binders are pyridine oxides or heterocyclic nitrogen compounds, such as for instance: hydroxy-quinolin, picolinic acid, etc.

Nevertheless, apart from the chemical diversity of the above-mentioned organo-metal complexes of W or Mo, in comparison to the compositions of formula (I) of the present invention, their activity as catalysts in general turns out to be limited to homogeneous catalysts in one single reaction phase containing H$_2$O, H$_2$O$_2$, catalyst and olefine, dissolved in a homogeneous organic solvent medium common to all.

In fact, the olefine is in general insoluble in an aqueous phase and thus one operates with H$_2$O$_2$ at a high concentration (greater than 70%).

These earlier operational conditions entail extremely slow reaction speeds, a low productivity in the oxidized produt (epoxides, etc.) because of the limited solubility of H$_2$O$_2$ in the homogeneous solvent/olefine/catalyst system, or low conversions and low selectivity for the presence of hydrolysis products, etc.

Thanks to their characteristics of good solubility in the standard organic solvents and, in general, low or insignificant solubility in water, the compositions of formula (I) of the present invention are especially suited for use as epoxidation catalysts according to the phase-transfer technique.

Based upon presently available information, the applicants do not know of any prior art dealing with compositions based on tungsten and phosphorus or arsenic, containing active oxygen and "onium" cations of formula (I) as herein above defined, obtained according to the preparative process described further on.

One object of the present invention is, thus, that of providing a class of tungsten and phosphorus- or arsenic-based compositions, containing active oxygen and "onium" cations, having a useful application in oxidation reactions, and especially in the epoxidation of compounds with olefinic bonds, preferably carried out according to the so-called "phase-transfer" technique.

Another object of the present invention is that of providing a method for the preparation of the above-specified compositions.

These and still other objects, which will appear more clearly to those skilled in the art from the following description, are achieved, according to this invention, by the class of compositions of formula (I) as hereinabove defined and by the corresponding preparative process, characterized in that a suitable oxygenated tungsten derivative, a suitable oxygenated derivative of an element chosen from amongst P and As, and hydrogen peroxide, contained in an aqueous acid phase, are made to react with an "onium" salt or with a precursor thereof, if desired while contained in an organic phase immiscible with the aqueous phase.

From the resulting reaction mass the composition is isolated according to conventional methods, for instance by separation of the organic phase, filtration of said organic phase, and evaporation of the filtrate.

More explicitly, the compositions of the present invention are prepared by the reaction between a suitable oxygenated tungsten compound, a suitable oxygenated phosphorus or arsenic compound, and hydrogen peroxide, all contained in an acid aqueous phase, with an "onium" salt, if desired contained in an organic, substantially water-immiscible solvent, according to predetermined, even if not critical, molar ratios, under conditions of substantially atmospheric pressure and at a temperature preferably between about 20° C. and about 80° C., but at most between about 0° C. and about 100° C.

In the preparation of the compositions of formula (I) there are used oxygenated W (VI) compounds, such as tungstic acid or the corresponding salts of alkaline metals.

In general, however, there may be used any derivative of W or tungsten itself, which derivative or metal, under the desired reaction conditions, may give rise "in situ" to the above said oxygenated W (VI) derivatives. Thus, there may be used for instance: $WO_2$, $W_2O_5$, $WO_3$, $WS_2$, $WS_3$, W oxychloride, W chloride, W-hexacarbonyl, etc.

Analogously, in the reaction there are used oxygenated compounds of P (V) or of As (V), such as for instance phosphoric acid, arsenic acid and their alkali metal salts, such as the sodium or potassium salts.

Also in this case, however, there may be used any one of the P or As derivatives, which derivative may, under the desired reaction conditions, give rise "in situ" to the phosphate or arseniate ion.

There may thus be used, for instance, $P_2O_5$, $As_2O_5$, $PCl_5$, $AsCl_5$, $POCl_3$, $AsOCl_3$, or polyphosphoric acid. There may also be used water-soluble salts containing As and W, or P and W, for instance those of aresnotungstic and phosphotungstic acids.

The "onium" salts consist of quaternary salts known per se, and responding to formula (II):

$$(R_1, R_2, R_3, R_4M)^+Y^- \qquad (II)$$

wherein:
M represents a pentavalent element belonging to the VA Group of the Periodic System;
$Y^-$ represents a stable inorganic anion such as $Cl^-$, $HSO_4^-$, $NO_3^-$, etc.;
$R_1$, $R_2$, $R_3$ and $R_4$, either equal to or different from each other, represent hydrogen or hydrocarbon monovalent groups having a total number of carbon atoms of up to 70, but preferably between 25 and 40, for applicational reasons as will be more clearly indicated further on.

Depending on whether M is an N, P, As, or Sb atom, one will get the corresponding "onium" salts, i.e., ammonium (N), phosphonium (P), arsonium (As), or stibonium (Sb) salts.

As an "onium" salt source there may, moreover, be used "onium" salts, preferably chlorides, immobilized on macroporous polymeric matrices of the polystyrenic or silicone type, which matrixes are preprable according to known techniques of the prior art and/or are available on the market.

The compositions obtained with the "onium" salts fixed on polymeric matrices, are useful as epoxidation catalysts for olefines.

Thus, an object of the present invention is also the provision of epoxidation catalysts fixed on macroporous polymeric polystyrenic or silicone resins, characterized in that said catalysts are prepared by reaction of an oxygenated tungsten derivative, an oxygenated derivative of an element chosen from amongst P and As, and hydrogen peroxide, contained in an aqueous acid phase with an "onium" salt fixed on a macroporous polymeric polystyrenic or silicone resin.

In this preparative process the pH of the aqueous phase is preferably lower than 4, but more preferably below 2, while usually it is not below zero.

The exact structure of these catalysts fixed on resins has not been established. For simplicity's sake, in the following they will be indicated as "catalysts fixed on resins".

The catalysts fixed on resins are insoluble in aqueous and organic solvents and, thus, prove to be particularly effective in the triple organic liquid/aqueous liquid/solid phase. They prove particularly interesting because of the possibility of their recovery at the end of the reaction, thanks to their insolubility.

Lastly, in the process for the preparation of the compositions of formula (I), the ammonium quaternary salts, for M=N in formula (II), as herein above defined, may be replaced by the equivalent primary, secondary and tertiary amines, which in the existing reaction system may give place to quaternized species.

As organic solvents for the "onium" salt there are used, in general, in the preparative process of formula (I) compositions, inert solvents substantially immiscible with the aqueous phase containing the W/P or W/As compound, and capable of solubilizing the reaction product.

Particularly suited for the purpose prove to be the aromatic hydrocarbons such as benzene, toluene, xylenes, etc., and the chlorinated hydrocarbons such as dichloromethane, dichloroethane, trichloroethane, chlorobenzene, etc.

In the preparation of the compositions of formula (I) of the present invention, the pH value of the aqueous phase, containing hydrogen peroxide and the soluble oxygenated W- and P- or As- derivatives, is maintained under 4 and, preferably, under about 2. Commonly, the pH value is adjusted, if required, by means of mineral acids.

As far as the molar ratios of the reactants are concerned, they are not critical with respect to the formation of composition (I), but the following ratios represent, however, operational values that have been found to ensure advantageous results as far as yield and purity of product are concerned.

There are thus preferably used, for each mol of P or As compound, expressed as P or As, at least 4 mols of the W compound, expressed as W, and up to 2 mols of "onium" salt.

The above-indicated values are optimal values, and while greater quantities of P or As compound do not bring any advantage, greater quantities of "onium" salts cause a gradual drop in the purity.

As far as the $H_2O_2$ is concerned, from about 2.5 to about 6 mols per each mol of W (VI) compound suffice. Greater values are compatible though not advantageous. In case W compounds are used with a valency below VI, to the above said quantity of $H_2O_2$ there must also be added the quantity necessary for bringing the W to the state of oxidation VI.

The concentration of the reactants in the aqueous as well as in the organic phase, does not represent a critical parameter and the same holds true for the reaction times.

The compositions of formula (I) according to the present invention show up either in the physical state of crystallizable solids or as thick oily liquids.

In general, they prove soluble in conventional organic solvents, such as for instance, alcohols, ketones, chlorinated hydrocarbons, aromatic hydrocarbons, etc., such as methyl alcohol, ethyl alcohol, etc.; acetone, ethylmethylketone, etc.; methylene chloride, dichloroethane, etc.; benzene, toluene, xylenes, etc.

On the contrary, compositions (I) prove to be little soluble or insoluble in water, directly dependent on the number of carbon atoms and/or of the nature of the radicals from $R_1$ to $R_4$ of the "onium" salt used; the solubility in water rises considerably in the case of salts with a low total number of carbon atoms, say, of the order of 20 atoms.

Lastly, the compositions prove to have active oxygen, which makes them particularly suited for the applications previously illustrated.

According to an effective operational form, the compositions of formula (I) are obtained in the following way:

The oxygenated W (VI) derivative (for instance tungstic acid) and the oxygenated derivative of P (V) or of As (V) (for instance phosphoric acid or arsenic acid), in the predetermined molar ratios, either in an aqueous suspension or solution having a pH value (possibly corrected with a mineral acid) below 2, are treated, under stirring, with an aqueous $H_2O_2$ solution in the desired ratio, at a temperature between about 20° C. and about 80° C.

Then, under stirring, there is admixed, preferably at room temperature, the predetermined quantity of "onium" salt dissolved in an organic solvent (dichloroethane, benzene, etc.) immiscible with water.

The resulting biphasic mixture is kept under stirring for between 15 and 30 minutes. If the product thus formed appears in the solid sate, it will be directly separated from the biphasic mixture by filtering, etc. In the contrary case, the organic phase will be separated and filtered and then evaporated under vacuum at a temperature of 40°–50° C., thereby obtaining the composition of formula (I) in the form of either a solid or a thick oil.

Or else, in the presence of "onium" salts particularly soluble in $H_2O$, it is possible to operate in one single aqueous phase. In this case, the separation of the product is achieved by filtering (if solid) or by extraction with solvents of the aqueous phase, etc. (if oily).

In their turn, the catalysts fixed on resins are obtained by treating in an acid aqueous phase the compound of W (e.g., tungstic acid) and of As (e.g., arsenic acid) or of P (e.g., phosphoric acid), with $H_2O_2$, as previously above-described at a temperature preferably between 20° and 80° C. Thereupon there is added the organic solvent (e.g., toluene) and the "onium" salt on a polymer, preferably in the form of a chloride, carrying on the stirring for about 2 hours at a temperature between about 60° and about 100° C. The catalyst fixed on resin is then separated, e.g., by filtering.

As indicated previously, the compositions of formula (I) and the catalysts fixed on resins of the present invention, when used as epoxidation catalysts for olefines, may be used according to phase transfer catalysts aqueous liquid-organic liquid with catalyst (I) or aqueous liquid/organic liquid/solid, with the catalyst fixed on the resin.

Compositions of formula (I) may, furthermore, be supported, in a conventional way, on porous inert solid materials, such as for instance, clays, bauxites, Kieselguhr, alumina, pumice, zeolites, etc. The supporting is achieved according to conventional methods by successive impregnations of the support with solutions containing composition (I), according to composition (I)/support ratios within a wide range, i.e., for instance, between about 0.01:1 and about 0.05:1 by weight.

The oxidization reactions in which it is possible to use as catalysts compositions (I) either as oxidizing agents or as catalysts, or the catalysts fixed on resins, include the epoxidation of olefines, as indicated above, the oxidization of sulphides to sulphoxides, etc.

More particularly, the compositions having formula (I) and the catalysts fixed on resins, as indicated above, find their most effective application as epoxidation catalysts for olefinic compounds with $H_2O_2$ as oxidizing agent, according to the aqueous liquid/organic liquid or the aqueous liquid/organic liquid/solid or the aqueous-organic liquid/solid technique.

In the case of the epoxidation reaction of olefines with $H_2O_2$ catalyzed by the compositions (I) of the recent invention, one operates in a phase-transfer system, in general aqueous liquid/organic liquid, essentially consisting of:

(a) an organic phase substantially containing catalyst (I) of the present invention, the olefine to be epoxidized, and the possible solvent, and (b) an aqueous phase containing substantially the $H_2O_2$.

Or else, the catalyst fixed on resin or catalyst (I) on a support may form a third solid phase (c).

The use as catalysts of compositions (I) and of the catalysts fixed on resins of this invention, according to the above-indicated technique, enables one to use the $H_2O_2$ in a much diluted form, even at a titre below 10%, and to obtain at the same time a high conversion rate of the $H_2O_2$ itself, combined with a high selectivity in the epoxide of the olefine, without the necessity, encountered in prior art processes, to homogenize the system with the use of suitable solvents and, above all, without requiring recourse to any of the burdensome operations for the removal of the water from the reaction medium.

Thus, the aspect that best characterizes the compositions (I) and the catalysts fixed on resins of the present invention, when applied in reactions of this type, is that, on the one hand, they ensure results superior to those obtainable with the best catalytic systems based on organometal compounds with active oxygen, acting in a homogeneous or heterogeneous phase, and on the other hand, unlike the latter, they turn out to be exceptionally well suited for being used according to the above-said phase transfer technique, obtaining significant economical and operational advantages.

The epoxidation rection of the olefines, using as catalysts compositions (I) and the catalysts fixed on resins of the present invention, occurs preferably under the following operational conditions:

The epoxidation reaction, which may be represented by the following scheme:

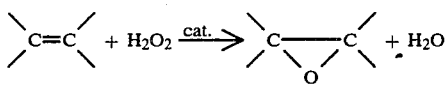

as said above, is conducted in a two-phase aqueous/organic system, under vigorous stirring, in the presence of catalyst (I) of the present invention, as hereinabove defined.

The organic phase contains the olefine and a possible organic solvent, while the aqueous phase contains the hydrogen peroxide.

In the case of the use of the catalyst fixed on resin, the reaction is conducted under the same operational conditions; but in such a case in the presence of a three-phase aqueous liquid/organic liquid/solid system, as indicated above.

The operational temperature and pressure are practically determined by the reactivity and by the nature of the olefine and by the stability of the hydrogen peroxide and of the catalyst used.

Temperatures between 0° and 120° C., and pressures between atmospheric pressure and 100 atmospheres, are as a rule quite operationally sufficient.

The olefines which may be subjected to the epoxidationreaction according to the present invention, may be represented by the following formula:

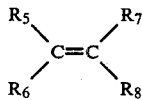

wherein: $R_5$, $R_6$, $R_7$ and $R_8$, optionally substituted with functional groups inert under reaction conditions, represent indifferently hydrogen atoms or hydrocarbon groups, such as alkyls and alkenyls having up to 30 carbon atoms, cycloalkyls and cycloalkenyls with from 3 to 12 carbon atoms optionally in the branched form, aryls, alkyl-aryls, alkenyl-aryls with from 6 to 12 carbon atoms; moreover, an $R_5$, $R_6$, $R_7$ or $R_8$ group, taken together with an adjacent group, may represent cyclic alkyl or alkenyl groups having up to 12 carbon atoms in the resulting ring.

Substituent groups, inert under reaction conditions, are, for instance, hydroxy, halogen (Cl, Br, F, I), nitro, alkoxy, amine, carbonyl, carboxylic, ester, amide, nitrile, etc. groups.

As indicated above, groups $R_5$, $R_6$, $R_7$ and $R_8$ may also be alkenyls; in other words, the process according to this invention is applicable also to polyolefines such as dienes, trienes, either conjugated or not.

Olefines suited for the epoxidation according to the present invention include, for exemplifying purposes; unsaturated alkyl, alicyclic, alkylaryl hydrocarbons such as propylene, butenes, pentenes, and in general the linear or branched mono- and di-olefines having up to 20 carbon atoms, cyclohexene, norborene, limonene, camphene, vinylcyclohexene, styrene, alphamethylstyrene, indene, stilbene, etc.; the unsaturated alkyl halides, such as the allyl halides; the unsaturated acids and their esters, such as the acrylic, methacrylic, crotonic, oleic, etc.; the unsaturated alcohols and their esters, such as allyl alcohol, etc.; the unsaturated aldehydes and the unsaturated ketones, etc.

The duration of the reaction depends on the nature of the catalyst and on the type of solvent and of olefine used; in general, duration times between just a few minutes and a few hours are quite sufficient for completing the reaction.

The catalyst is used in quantities between 0.0001 and 1 g/atom of the metal per 1 mol of hydrogen peroxide, but preferably between about 0.005 and about 0.05 g/atom per 1 mol.

There may furthermore be used mixtures of compositions (I). Mixtures of this type may be obtained, for instance, using commercial "onium" salt mixtures.

As already indicated above, the reaction is conducted under phase-transfer conditions, for instance, in a biphasic aqueous liquid/organic liquid system.

More particularly, organic phase (a) may be indifferently constituted of the same reacting olefine used in a suitable excess, or it may be constituted of the reacting olefine dissolved in organic solvents.

As solvents for the organic phase there are used inert solvents, substantially immiscible with the aqueous phase; effective practical results are obtained by using aromatic hydrocarbons such as benzene, toluene, xylenes, chlorinated hydrocarbons such as dichloromethane, trichloromethane, chloroethane, chloropropane, dichloroethanes, trichloroethanes, tetrachloroethanes, di- and trichloropropanes, tetrachloropropanes, chlorobenzene, alkyl esters, such as ethyl acetate, or suitable mixtures thereof.

The choice of the type of organic phase (a) is suggested to those skilled in the art, in each instance depending upon the reactivity of the starting olefine and on the parameters used for the reaction.

In the case in which in the organic phase there are used the above-described inert solvents, the concentration of the olefine in the solvent is not critical with regard to carrying out the process.

Suitable operational values of the concentration of the olefin in the organic phase are between about 5% and about 95% by weight, although both higher values or lower values are compatible within the limits of their practability.

The concentration of the hydrogen peroxide in the aqueous phase, lastly, may be maintained between about 0.1% and about 70% by weight. Nonetheless, the epoxidation reaction carried out with the catalysts of this invention offers the advantage of allowing one to operate with low concentration values for the hydrogen peroxide. Effective values of this concentration prove to be between 1% and about 10%; however, values lower than 1% are still operational. This brings about a favorable economical aspect of this invention in comparison with the costly preparation of the solutions with concentrations higher than 70% as used by the prior art, and the burdens for the operational safety already cited due to the necessity to maintain said high concentration throughout the course of the process.

The invention will now be further described by means of the following examples, given for purely illustrative purposes.

The yields have been calculated with reference to the quantity of "onium" salt used in the preparation of compositions (I) and of catalysts fixed on resins; w/v stands for weight/volume.

EXAMPLE 1

Into a beaker were placed:
2.50 grams of $H_2WO_4$ (10 mmols),
7 ml of $H_2O_2$ in a 30% concentration w/v (300 g/liter) (about 62 mmols).

The tungstic acid suspension was maintained under stirring at about 60° C. until complete dissolution of the tungstic acid.

After cooling down, the resulting colorless solution was additioned with 0.62 ml of a 40% w/v $H_3PO_4$ (400 g/liter) (2.5 mols).

The solution thus obtained was diluted with $H_2O$ to 30 ml, then filtered and introduced into a reactor fitted with a dripper and a stirrer. Under stirring, there were then dripped into the reactor, in about 2 min., 1.60 g of methyltrioctylammonium chloride (about 4 mmols) dissolved in 40 ml of methylene chloride.

After 15 minutes of further stirring, the organic phase was separated, filtered and evaporated under the vacuum at between 40° and 50° C.

In this way, there were obtained 2.82 g (95.9% with respect to the "onium" salt used) of a thick, colorless oil which, according to a percentual analysis, turned out to have the following formula:

$$C_{75}H_{162}N_3PW_4O_{22} = [(C_8H_{17})_3N\ CH_3]_3PW_4O_{22}$$

| Elementary Analysis | Theoretical % | Found % |
|---|---|---|
| C | 40.49 | 40.35 |
| H | 7.34 | 7.42 |
| N | 1.89 | 1.85 |
| P | 1.39 | 1.32 |
| W | 33.06 | 32.79 |

Active [0]found (determined by iodometry in acetic acid) =4.33%,
Active [0] theoretical (calculated for 6 $0_{act.}$)=4.315%,
Molecular weight (in $CHCl_3$)=2190 (theoretical=2224.7).

EXAMPLE 2

The procedure was as in Example 1, but substituting the methyltrioctylammonium chloride with 1.56 g of tetrahexylammonium chloride (about 4 mmols) dissolved in 40 ml of benzene.

From the resulting biphasic mixture there was then directly separated a white solid which was filtered, washed with $H_2O$, then washed with a little benzene, and finally dried on a porous plate.

Thereby were obtained 2.35 g (80.8%) of a product which, according to a percentual analysis, proved to be of the formula:

$$C_{72}H_{156}N_3PW_4O_{22} = [(C_6H_{13})_4N]_3PW_4O_{22}$$

| Elementary Analysis | Theoretical % | Found % |
|---|---|---|
| C | 39.62 | 39.17 |
| H | 7.20 | 7.19 |
| N | 1.92 | 1.90 |
| P | 1.42 | 1.44 |
| W | 33.70 | 33.57 |

Active [0]found=4.42%; theoretical active [0](calculated for 6 $0_{act.}$)=4.40%,
Molecular weight (in $CHCl_3$)=2210 (theoretical=2182.6).

EXAMPLE 3

The procedure was as in Example 2, but substituting the $H_3PO_4$ with 0.78 g of $NaHAsO_4.7H_2O$ (2.5 mmols) dissolved in 3-4 cc of $H_2O$ and acidified with 3.5 ml of $H_2SO_4$ at a 30% concentration.

From this biphasic mixture there was thereupon directly separated a white solid which was filtered, washed first with $H_2O$ and then with a little benzene, and finally dried on a porous plate.

Thereby were obtained 2.4 g (79.7%) of product, which, according to a percentual analysis, proved to be of the formula:

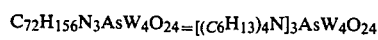

$$C_{72}H_{156}N_3AsW_4O_{24} = [(C_6H_{13})_4N]_3AsW_4O_{24}$$

| Elementary Analysis | Theoretical % | Found % |
|---|---|---|
| C | 38.29 | 38.36 |
| H | 6.96 | 6.97 |
| N | 1.86 | 1.89 |
| As | 3.32 | 3.24 |
| W | 32.57 | 32.57 |

Active [0]found=5.61%
Active [0]theoretical (calculated for 8 $0_{act.}$)=5.67%.
Molecular weight (in $CHCl_3$)=2200 (theoretical=2258.6).

EXAMPLE 4

The procedure was as in Example 1, but substituting the methyltrioctylammonium chloride with 1.36 g of tetrabutylammonium bisulfate (about 4 mmols) dissolved in 15 ml of $H_2O$ instead of in an organic solvent immiscible with water, and thus operating in one single aqueous phase.

The precipitated white solid was thereupon filtered, washed with a little $H_2O$ (10 ml) and then dried on a porous plate.

Thereby were obtained 2.2 g (87.8%) of product, which turned out to be partially soluble in $H_2O$ and very soluble in the conventional solvents (dichloroethane, acetone, $CH_2Cl_2$, etc.) and which, according to the percentual analysis, turned out to have the following formula:

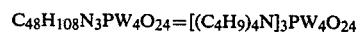

$$C_{48}H_{108}N_3PW_4O_{24} = [(C_4H_9)_4N]_3PW_4O_{24}$$

| Elementary Analysis | Theoretical % | Found % |
|---|---|---|
| C | 30.70 | 30.74 |
| H | 5.80 | 5.82 |
| N | 2.24 | 2.23 |
| P | 1.65 | 1.59 |

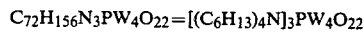

| Elementary Analysis | Theoretical % | Found % |
|---|---|---|
| W | 39.17 | 39.34 |

Found active [0] = 7.76%;
Theoretical active [0](calculated for 8 $0_{act.}$) = 6.815%,
Molecular weight (in $CH_2Cl_2$) = 1930 (theoretical = 1878).

EXAMPLE 5

The procedure was as in Example 1, but substituting the $H_3PO_4$ with 0.78 g of $Na_2HAsO_4.7H_2O$ (2.5 mmols) dissolved in 3–4 ml of $H_2O$ and acidified with 3.5 ml of $H_2SO_4$ in a 30% concentration.

Thereby were obtained 2.76 g (93.5%) of a waxy product which, according to the percentual analysis, proved to have the following formula:

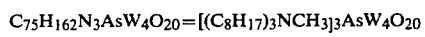

$C_{75}H_{162}N_3AsW_4O_{20} = [(C_8H_{17})_3NCH_3]_3AsW_4O_{20}$

| Elementary Analysis | Theoretical % | Found % |
|---|---|---|
| C | 40.27 | 40.47 |
| H | 7.30 | 7.32 |
| N | 1.88 | 1.89 |
| As | 3.35 | 3.40 |
| W | 32.69 | 32.60 |

Found active [0]found = 2.75%;
Theoretical active [0](calculated for 4 $0_{act.}$) = 2.86%,
Molecular weight (in $CHCl_3$) = 2225 (theoretical = 2236.6).

EXAMPLE 6

The procedure was as in Example 4, but substituting the $H_3PO_4$ with 0.78 g of $Na_2HAsO_4.7H_2O$ (2.5 mols) dissolved in 3–4 ml of $H_2O$ and acidified with 3.5 ml of $H_2SO_4$ in a 30% concentration.

Thereby were obtained 2.18 g (84.8%) of a white solid which, according to the percentual analysis, turned out to be of the formula:

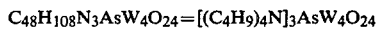

$C_{48}H_{108}N_3AsW_4O_{24} = [(C_4H_9)_4N]_3AsW_4O_{24}$

| Elementary Analysis | Theoretical % | Found % |
|---|---|---|
| C | 29.99 | 29.67 |
| H | 5.66 | 5.61 |
| N | 2.19 | 2.17 |
| As | 3.90 | 3.85 |
| W | 38.28 | 38.30 |

Found active [0]found = 6.60%;
Theoretical active [0](calculated for 8 $0_{act.}$) = 6.66%.

EXAMPLE 7

Into a beaker were placed:
3.30 g of $Na_2WO_4.2H_2O$ (10 mmols),
30 ml of $H_2O$,
0.55 g of $NaH_2PO_4.H_2O$ (4 mmols).

This solution was thereupon acidified with $H_2SO_4$ in a 30% concentration until a pH = 1 was reached, thereupon there were admixed with it 3 ml of $H_2O_2$ at a 40%w/v concentration (about 35 mmols).

To the resulting filtered solution was added tetrahexylammonium chloride (1.56 g), proceeding as in Example 2.

Thereby were obtained 2.30 g (79%) of a white solid which corresponded to the produce of Example 2.

EXAMPLE 8 (catalyst fixed on a resin)

Into a beaker were placed:
14 g of $H_2WO_4$ (56 mmols),
39 ml of $H_2O_2$ in a 30% w/v concentration 344 mmols).

The suspension of tungstic acid was maintained under stirring at about 60° C. until the full dissolution of the tungstic acid was achieved. After cooling down, the resulting colorless solution was additioned with 3.45 ml of $H_3PO_4$ at a 40% w/v concentration (14 mmols).

The solution was thereupon diluted to 120 ml with $H_2O$ and then filtered. There were then added 40–50 ml of toluene.

Into the mixture thus obtained, there were then introduced as an "onium" salt 8.75 g of hexyltributylphosphonium chloride supported on a polystyrenic matrix (0.62 milliequivalents of $Cl^-$/1 g of resin) and the whole was then heated under vigorous stirring at 80° C. for 2 hours.

The resin was then filtered, washed with a little water and then with toluene, after which it was dried on a porous plate.

Thereby were obtained 11.6 g of a resin containing 15.5% of tungsten.

EXAMPLE 9

Into a 4-necked reactor of 250 ml holding capacity, fitted with a blade stirrer, a thermometer and a reflux coolant, there were introduced 15 ml of $H_2O$, 10.5 ml of $H_2O_2$ in a 40.14% w/v concentration (corresponding to about 124 mmols), 1.41 g of the composition of Example 1 (corresponding to 2.53 mmols of W) dissolved in 20 ml of 1,2-dichloroethane and 31 ml of 1-octene (about 200 mmols).

The mixture was then quickly brought up to 70° C. under vigorous stirring and was then maintained at this temperature for 45 minutes. At the end there were metered by iodometry 1.24 mmols of unreacted $H_2O_2$ in the aqueous phase and by gas chromatography 109.2 mmols of 1,2-epoxyoctane in the organic phase, which corresponded to a conversion of the hydrogen peroxide of 99% with a selectivity in epoxide on the consumed hydrogen peroxide equal to 89%.

EXAMPLE 10

The same procedure was followed as in Example 9, but using 1-dodecene (44.3 ml; about 200 mmols) instead of 1-octene. At the end there were metered 1.74 mmols of unreacted $H_2O_2$ (conversion: 98.6%) and 116.6 mmols of 1,2-epoxydodecane (selectivity: 95% calculated on the consumed $H_2O_2$).

EXAMPLE 11

The same procedure was followed as in Example 9, but using allyl chloride (32.8 ml; about 400 mmols) instead of 1-octene, benzene (30 ml) instead of 1,2-dichloroethane, and operating at 60° C. (temperature of the bath) for 3 hours.

At the end there were metered 0.75 mmols of unreacted $H_2O_2$ (conversion:99.4%) and 99.8 mmoles of epichlorohydrin (selectivity: 81% on the $H_2O_2$).

EXAMPLE 12

The procedure was followed as in Example 9, but using the composition of Example 3 (2 g corresponding to 3.54 mmols of W) instead of the composition of Example 1.

At the end there were metered 1.24 mmols of unreacted $H_2O_2$ (conversion: 99%) and 110.5 mmols of 1,2-epoxyoctane (selectivity: 90% on the $H_2O_2$).

EXAMPLE 13

Operation was as in Example 1, but substituting the methyltrioctylammonium chloride with 2.30 g of dimethyl [dioctadecyl (75 %) - dihexadecyl (25%)]ammonium chloride (ARQUAD 2HT produced by AKZO Chemie Italia S.p.A.), having an average formula: $C_{37}H_{38}NCl$, (about 4 mmols) dissolved in 40 ml of methylene chloride.

By evaporation of the organic phase (preliminarily filtered on paper) at 40°-50° C. under vacuum, there were obtained 3.40 g (93% with respect to the "onium" salt used) of a white solid which, according to the precentual analysis, proved to have the following average formula:

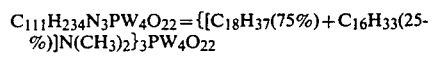

$C_{111}H_{234}N_3PW_4O_{22} = \{[C_{18}H_{37}(75\%) + C_{16}H_{33}(25\%)]N(CH_3)_2\}_3PW_4O_{22}$

| Elementary Analysis | Theoretical % | Found % |
|---|---|---|
| C | 48.84 | 48.79 |
| H | 8.64 | 8.74 |
| N | 1.54 | 1.53 |
| P | 1.135 | 1.15 |
| W | 26.95 | 26.75 |

Found active [0]found = 3.51%
Theoretical active [0](calculated for 6 $0_{act.}$) = 3.52%
Average molecular weight (in 1,2-dichloroethane) = 2940 (theoretical:2729.68).

EXAMPLE 14

The procedure of Example 9 was followed, but using the composition of Example 13 (1.71 g, corresponding to 2.5 mmols of W) instead of that of Example 1, using benzene (20 ml) instead of 1,2-dichloroethane, and prolonging the reaction time to 90 minutes.

At the end there were metered 18.6 mmols of unreacted $H_2O_2$ (conversion:85%) and 88 mmols of 1,2-epoxyoctane (selectivity: 83.5% on the $H_2O_2$ consumed).

EXAMPLE 15

Operation was as in Example 1, but substituting the methyltrioctyl-ammonium chloride with 1.25 g of triphenylmethylphosphonium chloride(4 mmoles) dissolved in 40 ml of methylene chloride.

By evaporation of the organic phase (preliminarily filtered on paper) at 45°-50° C. under vacuum, there was obtained a white solid which, according to the percentual analysis, proved to have the following formula:

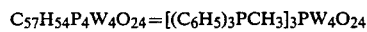

$C_{57}H_{54}P_4W_4O_{24} = [(C_6H_5)_3PCH_3]_3PW_4O_{24}$

| Elementary Analysis | Theoretical % | Found % |
|---|---|---|
| C | 34.53 | 34.49 |
| H | 2.75 | 2.90 |
| P | 6.25 | 6.40 |
| W | 37.10 | 36.80 |

Active [0]found = 6.33%
Theoretical active [0](calculated for 8 $0_{act.}$) = 6.46%
Molecular weight (in 1,2-dichloroethane) = 2120 theoretical = 2182.6).

EXAMPLE 16

Example 9 was repeated, but using the composition of Example 5 (1.4 g, corresponding to 2.5 mmols of W) instead of the composition of Example 1, and reducing the reaction time to 35 minutes.

At the end there were metered 0.75 mmols of unreacted $H_2O_2$ (conversion: 99.4%) and 99.1 mmols of 1,2-epoxyoctane (selectivity: 80.3% on the $H_2O_2$).

EXAMPLE 17

Example 9 was repeated, but, instead of the composition of Example 1, there was used the catalyst supported on a polystyrenic matrix of Example 8 (9 g of resin, corresponding to about 8 mmols of W), and prolonging the reaction time to 2 hours.

At the end there were metered 1.74 mmols of unreacted $H_2O_2$ (conversion: 98.6) and 97.8 mmols of 1,2-epoxyoctane (selectivity: 80% on the $H_2O_2$).

EXAMPLE 18

To 11.3 g (corresponding to about 5.1 mmols) of the composition of Example 1, dissolved in 35 ml of benzene, there were added 25 ml of cyclohexene (about 200 mmols).

This mixture, kept under stirring, was brought up to 70° C. and maintained at this temperature for 1 hour.

At the end there were metered by gas chromatography 1.93 g (19.7 mmols) of epoxycyclohexane.

EXAMPLE 19

The procedure was as in Example 18, but using 1-octene (31 ml; about 200 mmols) instead of cyclohexene.

At the end there were metered by gas chromatography 2.93 g (22.9 mmols) of 1,2-epoxyoctane.

What is claimed is:

1. An epoxidation catalyst for olefines, fixed on a polymeric macroporous polystyrenic or silicone resin, characterized in that said catalyst is prepared by reaction of an oxygenated derivative of tungsten, an oxygenated derivative of an element chosen from amongst P and As, and hydrogen peroxide, contained in an acid aqueous phase, with an "onium" salt fixed on a macroporous polymeric polystyrenic or silicone resin.

2. A process for the preparation of an epoxidation catalyst fixed on a polymeric macroporous polystyrenic or silicone resin according to claim 1, characterized in that an oxygenated tungsten derivative, an oxygenated derivative of an element chosen from amongst P and As, and hydrogen peroxide, contained in an aqueous phase having a pH below 4 are reacted with an "onium" salt fixed on a polymeric macroporous polystryenic or silicone resin.

* * * * *